United States Patent [19]

Brawner

[11] Patent Number: 4,822,342
[45] Date of Patent: Apr. 18, 1989

[54] PREPARED TAPE FOR BODY INSERTED TUBE

[76] Inventor: Johnny A. Brawner, 5291 W. 229th St., Fairview Park, Ohio 44126

[21] Appl. No.: 442,631

[22] Filed: Nov. 18, 1982

[51] Int. Cl.[4] ............................................ A61M 25/02
[52] U.S. Cl. ............................ 604/180; 128/DIG. 26
[58] Field of Search .......... 128/133, DIG. 26, 207.18; 604/174, 179, 180

[56] References Cited

U.S. PATENT DOCUMENTS

| | | | |
|---|---|---|---|
| 3,677,250 | 7/1972 | Thomas | 604/180 |
| 3,826,254 | 7/1974 | Mellor | 604/180 X |
| 3,834,380 | 9/1974 | Boyd | 604/180 X |
| 3,918,446 | 11/1975 | Buttaravoli | 604/180 X |
| 4,057,066 | 11/1977 | Taylor | 128/DIG. 26 |
| 4,324,237 | 4/1982 | Buttaravoli | 604/180 |
| 4,333,468 | 6/1982 | Geist | 604/180 |
| 4,445,894 | 5/1984 | Kovacs | 604/179 |
| 4,484,914 | 11/1984 | Brown | 604/180 |

*Primary Examiner*—Dalton L. Truluck
*Attorney, Agent, or Firm*—Albert L. Ely, Jr.

[57] ABSTRACT

Prepared tape for securing devices, such as inserted intravenous needles, catheters, and/or associated tubing and tubing components comprising lengths of a base tape and an anchoring tape, each having a pressure sensitive surface and a nonadherent backing, the backings being joined together so that at least one segment of the anchoring tape's adhesive surface can be wrapped onto the device to be secured by adhesion of the base tape to a patient's skin or a support. The adhesive surfaces of the tapes are covered prior to use by release materials provided with pull-tabs. An edge of the base tape is preferably idented to stabilize the patient's skin adjacent the point of entry of an inserted needle.

13 Claims, 2 Drawing Sheets

PREPARED TAPE FOR BODY INSERTED TUBE

This invention relates to improvements in prepared surgical tapes for quickly securing inserted needles and associated tubing, catheters, and the like with minimal paint or distraction to the patient and time and concern of physicians and attending nurses. This invention also relates to a method of manufacturing such prepared tapes inexpensively by conventional web-converting apparatus.

In post-operative, pre-operative, or other care (for example, the transfusion or donation of blood, intravenous feeding, or the supply of sera or other liquids), treatment of the patient often requires that liquids be supplied to or withdrawn from the patient's body over a substantial period of time. This is accomplished by means of catheters or often by hypodermic needles connected by tubing to a suitable supply reservoir or receptacle for discharge.

The affixing of such needles, catheters, or like devices to a patient is preferably done quickly to minimize both the duration of the initial degree of trauma to the patient and the time required by the attending physician and staff. The fixation must be secure in order to avoid dislodging the device from the desired position without undue restraint of the patient's movements and to avoid imposing on the attendant nurses or interns, who later check the patient from time to time, the emergency of attempting to reposition such a dislodged device while waiting for corrective action by a qualified physician.

The need for a prepared surgical device which can quickly and securely anchor an inserted needle or catheter to a patient has long been recognized and many attempts to satisfy that need have been made. However, as far as I am aware, none have met that need. Such devices often embody a relatively rigid member of molded plastic or the like adapted for snap-in reception of a tube or needle having specific configurations and dimensions and, therefore, are very limited in practical applications; others require excessive manipulation of their components, which can be disturbing to the patient and time-consuming for the physician and/or his staff; none are readily manufactured by conventional web-converting apparatus and, thus, are too expensive in view of the vast quantities required for both in-patient and out-patient care. Many such prior devices are also bulky, and, thereby, when packaged, unsatisfactory for maintenance of an adequate inventory in the available, but limited, storage space in hospitals. In hospital supply warehouses, the cost of storage space alone, added to the purchase price of a bulky item that should be sold as a low-cost item, can make the item uneconomical to keep in inventory in substantial quantities.

It is an object and advantage of this invention to provide a prepared surgical tape which overcomes the above summarized disadvantages of prior art devices. Other objects and advantages should be apparent from the following specification, claims, and drawings, in which:

Figure 1:
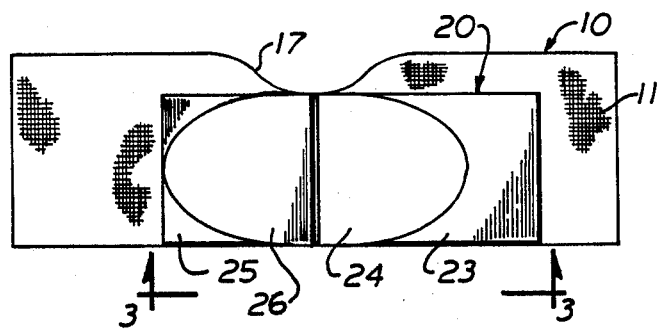
FIG. 1 is a plan view of a prepared tape made according to this invention, showing the anchoring tape uppermost.
Figure 6:
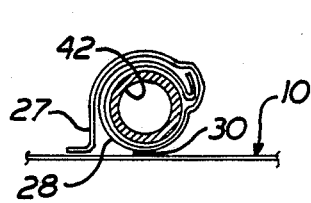
Figure 7:
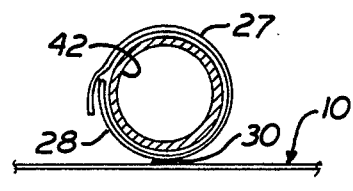
Figure 8:
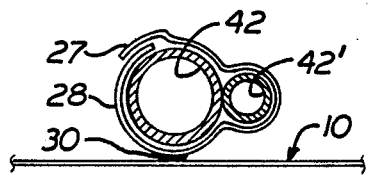
Figure 9:
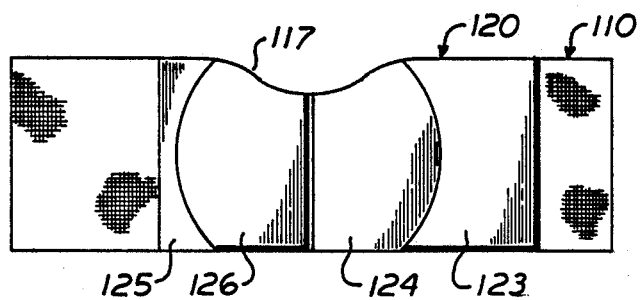

FIGS. 6, 7, and 8 are diagramatic views, i.e., with the adhesive strata omitted, showing the wraps of the segments of the anchoring strip around, respectively, a tube of relatively small diameter, a relatively large tube, and a double tube comprised of a smaller tube and a larger tube;

FIG. 9 is a plan view corresponding to FIG. 1 but showing a modification in which the width of the anchoring tape is equal to the width of the base tape.

Figure 2:
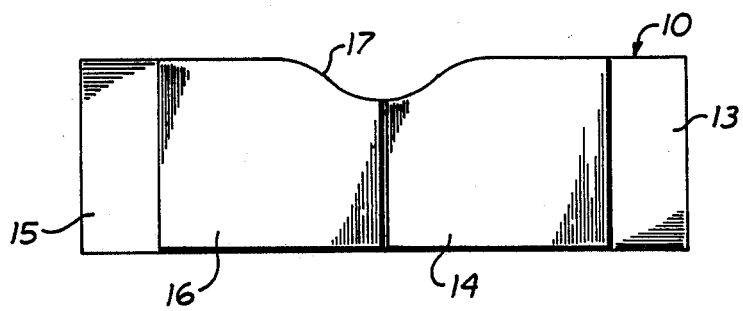
FIG. 2 is a bottom view of the prepared tape shown in FIG. 1.
Figure 3:
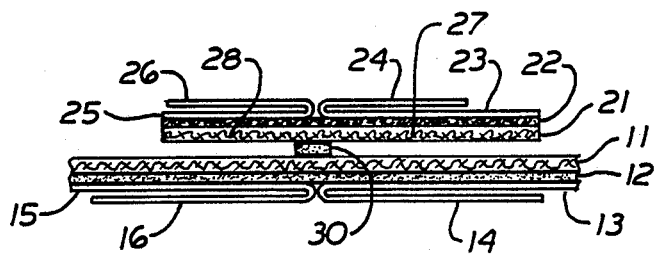
FIG. 3 is a side view, taken from the line 3—3 of FIG. 1. In this view, for the purposes of illustration, thicknesses are exaggerated and the several strata are, except for the release strips and pull-tabs, shown as though they were in section in order to indicate the materials of the strata.

Referring to FIGS. 1 to 3 of the drawing (showing a preferred embodiment of this invention), in FIG. 1 the reference number 10 represents a base tape, namely, a strip of conventional surgical adhesive tape comprised of a woven fabric backing 11 carrying on its normal under-surface a pressure-sensitive adhesive coating 12. The coating 12 is conventionally formulated and applied so as to provide its desired tackiness for the human skin or other surfaces while preserving a greatly preferential adhesion or bonding of the coating 12 to the cloth backing 11. The transverse width to length of the base tape 10 (as shown in FIGS. 1 and 2) is optional for various applications but, in practice, a width of approximately 3" to a length of 1" has been found satisfactory in most practical applications. One transverse edge of the base 10 is provided at its approximately center-line with a relatively deep and sinuously curved scallop 17; the proportion of the total width to the maximum depth of the scallop is, likewise, optional, but in practice, a total transverse width approximately equal to the length of the base 10 and a maximum depth of approximately onefourth of the width has been found satisfactory in most practical applications.

The tacky coating 12 is protected prior to use by covering the coating with segments 13 and 15 of a release material (see FIG. 2). The release material is usually glassine or other coated paper having relatively slight adhesion to the coating. Each segment 13 and 15 of release material extends transversely to the centerline of the base tape 10, where the segment is folded back to provide a generous pull-tab 14 for the release segment 13 and similar pull-tabs 16 for the segment 15. If a folded-back pull-tab 14 or 16 does not extend transversely beyond the start of the scallop 17 (usually formed by the same die-cutting operation which forms the scallop in the transverse edge of the base 10), manipulation of the tape by the physician may be hampered; otherwise the transverse length of a pull-tab 14 or 16 is optional and may even be greater than the transverse length of the segment of release material 13 and 15 from which they are folded back. In practice, a transverse length of about an inch and a half for each pull-tab provides an adequate length for the physician to grasp and pull back in order to uncover the adhesive coating 12 for the adhesion to the skin of the patient, without disturbing the patient or the positioned needle or tube.

Attached in a back-to-back relationship with the base tape 10 is the actual anchoring tape 20 comprised of a strip of conventional surgical adhesive tape, preferably of a lesser transverse width and lesser longitudinal length than the base 10. The anchoring tape 20 is comprised of a woven fabric backing 21, preferably similar to the backing 11, and a pressure-sensitive adhesive coating 22 (preferably similar to the coating 12) which is bonded to the backing 21. The adhesive surface of the coating 22 is covered and protected prior to use by a pair of segments of release material 23 and 25, each having an ample folded-back pull-tab 24 and 26 sufficient in length to permit the tabs to be grasped in order to pull away the segments 23 and 25 to expose the coating 22. (See FIG. 3)

Preferably, as shown in FIG. 1, the segments 23 and its underlying portion of the tape 21 is longer than the segment 25 so that the line formed where the folded-back pull-tabs 24 and 26 meet is off-center of the transverse width of the tape 20. That fold-back line is located over the center-line of the base tape 10 and joined by a narrow line of relatively flexible cement 30 (such as a collodion) which unites the base tape 10 and anchoring tape 20 in a substantially permanent cloth back-strip to cloth backingstrip relationship.

In the preferred embodiment shown in FIG. 1, not only is the anchoring tape 20 shorter in transverse width and mounted offcenter of the base tape, but (as shown in FIG. 1) the vertical length of the anchoring tape 20 is preferably no more than the length from the bottom of the scallop 17 to the lower transverse edge of the base tape 10.

To use the prepared tape as shown in FIGS. 1, 2, and 3 after an intravenous needle 40, with its attached tube 42, has been inserted up to nearly the hub 41 of the needle, the physician places the prepared tape, with the scallop 17 toward the subcutaneous entry of the needle, under the tube 42 and, with one hand, slips it toward the entry of the needle until the hub 41 over-lies the center-line of the base 10. While, with the fingers of one hand holding the base 10 and the needle by its hub 41 on the center-line of the base 10, one of the pull-tabs 14 or 16 is grasped with the fingers of the other free hand to peel away the attached segment of release material, allowing the portion of the thereby uncovered coating 12 to be immediately adhered to the patient's skin by pressing on the cloth surface with the fingers of the free hand. The similar removal of the other release segment then quickly secures all of the base 10 adhesively to the patient's skin. With the base 10 in place and the needle and tube held by the fingers of one hand, usually the adhesive 22 on the shorter anchoring segment 28 of the anchoring tape 20 is exposed by pulling away the release material segment 25 by means of the pull-tab 26 so that the segment 28 can begin to be wrapped around the needle hub while the hub and needle is held in place. As the shorter anchoring segment 28 is wrapped and the wrapped needle hub is held with one hand, the other hand is free to pull off the release segment 23 by means of the pull-tab 24, exposing the adhesive 22 on the longer anchoring segment 27, which, in turn, is then wrapped over the shorter anchoring segment 28; the greater length of the anchoring segment 27 usually allows its end to adhere to the cloth surface of the base 10. The flexibility of the fabric in the anchoring segments 28 and 27 allows them to conform to the contours of the wrapped needle hub (partly conical and partly cylindrical) so that, as shown in the upper portion of FIG. 4, the longer anchoring segment 27 may thereby be somewhat wrinkled where it is adhered to the cloth surface of the base tape 10, an immateriality in view of the secure adhesion of the base tape 10 to the patient and the anchoring of the needle hub 41 and the immediately adjacent connection of the hub with the supply tube 42.

The scallop 17 not only permits the adhesively secured base tape 10 to stabilize the skin of the patient adjacent and beyond the point of entry of the needle 40 but resists local lifting of the cloth backing 11 and adhesive 12 under the pulls and strains of conforming the wrapped anchoring segments 27 and 28 to the non-cylindrical configuration of the needle hub 41.

All of the foregoing manipulations of the base 10 and the anchoring segments 27 and 28, including the stripping away of the release material segments, are accomplished in a matter of seconds with minimal discomfort to the patient.

Figure 4:
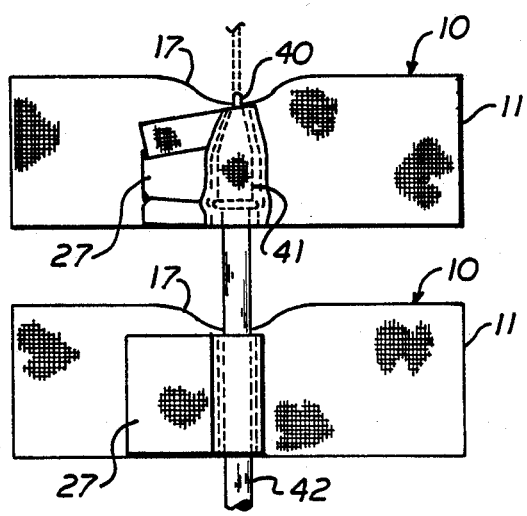
FIG. 4 is a plan view showing a prepared tape, made according to this invention, used to anchor the hub of an intravenous needle to the skin after it has been inserted into the patient's vein and another such tape used to secure to the patient's skin a supply tube connected to the needle's hub.

As indicated in the lower portion of FIG. 4, it is often preferable practice to another the supply tube 42 to the patient at least adjacent to the anchoring of the needle 40 and hub 41. This may be done by repeating the procedure as described above for anchoring the needle 40 and hub 41, not only adjacent to the anchoring of the needle and hub but elsewhere on the body of the patient. Prepared tapes made according to this invention are also frequently similarly used to anchor other portions of the tube 42, such as to portable stands carrying a supply bottle for the liquid being used for treatment and/or the valve by which the flow of such liquid is regulated as well as the sight tube by which the rate of flow can be observed.

Figure 5:
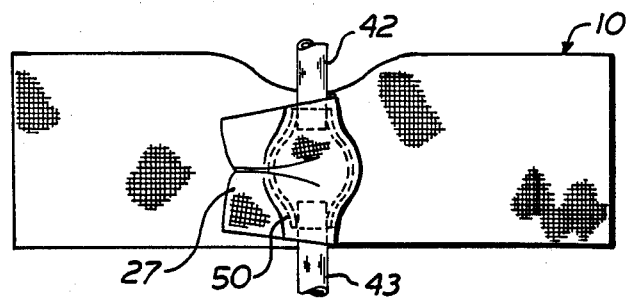
FIG. 5 is a plan view showing the base strip adhered to a patient's skin and the anchoring strip wrapped around a conventional fusiform tube connector.

Prepared tapes made according to this invention can be used to secure and anchor other items, such as fixtures or appurtenances used in the systems for the injection and/or withdrawal of liquid in the treatment of patients, regardless of the unusual configuration of such items. For example, as shown in FIG. 5, a supply tube 42 may need to be connected to another tube 43, either to permit, without disturbing the inserted needle 40, the supply of another liquid to the needle or simply to lengthen the supply tube 42. The conventional tube-connector 50 has the bulbous fusiform shape illustrated in FIG. 5; with the connector 50 held so that it overlies the center-line of the base tape 10, the release segments 23 and 25 are pulled away to expose the adhesive 22 and the shorter and longer anchoring segments 27 and 28 are then wrapped around the connector 50 so as to conform to its shape. Whether the base tape 10 is adhered to a convenient supporting surface by removal of the release segments 13 and 15 to expose the adhesive 12 before or after the connector 50 is anchored to the base tape 10 is optional.

Prepared tapes made according to this invention can accommodate a wide variety of tubes, as diagrammatically illustrated in FIGS. 6, 7, and 8. Thus, in FIG. 6, if the tube 42 is of a small diameter, the adhesive 22 is exposed by removing the release segmenets 23 and 25, the shorter anchoring segment 28 is adhered to the tube and if its length should be greater or nearly greater than the circumference of the tube 42, its end will be turned back when the longer anchoring segment 27 is over-wrapped and adhered to the base tape 10.

If the tube 42 is of a relatively larger diameter, as shown in FIG. 7, the shorter anchoring segment 28 is adhered partly around the tube and then the longer anchoring segment 27 is wrapped and adhered to the remaining exposed surface of the tube 42 and may overlap, as shown, the end of the segment 28. If the diameter of the tube 42 is so large that the anchoring segment 27 does not over-lap the segment 28, at least a sufficient portion of the surface of the tube 42 will usually be held by the anchoring segments 20 to be firmly anchored to the base tape 10 without requiring the addition of a short length of conventional surgical adhesive tape to cover a possible gap between, and thereby join, the ends of the segments 27 and 28.

As indicated in FIG. 8 tubing to double needles or double catheters may comprise of a pair of parallel tubes, often of different diameters. As in the case of larger diameter tubes shown in FIG. 7, the anchoring segments 28 and 27 can be conformed to enwrap and anchor such multiple tubing.

The preferred form of my prepared tape can be manufactured with minor, if any, modifications of conventional web-converting machinery, as used in the bag-making and packaging industries, and in which webs are joined together as they are fed longitudinally through the feed and cutting rolls or dies of such machines.

Thus, to form the base tape 10, conventional adhesive surgical tape having a web-width equal to the transverse width of the base tape 10, is drawn off a supply roll. Two webs of release material are likewise drawn-off supply rolls, longitudingly folded, and then fed, with the folds adjacent, through pressure rolls which join the release material to the adhesive 12.

To form the anchoring tape 20, conventional surgical tape having a web-width equal to the width of the tape 20 is similarly drawn off a supply roll and folded webs of release material are, with their folds adjacent, similarly adhered to the adhesive 22. To provide the semi-oval pull tab 14 and 16, an edge of each of the webs of release material is cut by die-cutting edge rolls, usually prior to folding. Anchoring tape lengths are then cut and spotted, cloth-backing to cloth-backing, at regular intervals along the web of the base tape 10, to the center-line of which a line of an active and quick-setting cement has been applied. The web of base tape 10 is then passed through cut-off rolls or die-cutters which transversely sever successive lengths of the tape 10 while cutting out the scallop 17 from one edge of a severed tape length.

FIG. 9 illustrates a modification of the preferred embodiment shown in FIG. 1, in which the length of the anchoring tape 120 is equal to the length of the base tape 110. The slight disadvantage of this modification is that the greater length of the anchoring segments underlying the release material segments 123 and 125 may cause more bunching of such segments as they are wrapped around non-cylindrical surfaces, such as a needle hub or fusiform connector and, thus, a slightly greater time of the physician may be required in causing such segments to conform to the surface of such items to be anchored. Its advantage is that the base tape 110 and anchor tape 120 may be produced on conventional web-converting machinery at a greater production rate by eliminating the need for "spotting" severed lengths of the anchoring tape 120 at spaced intervals on the web from which the lengths of the base tape 110 are severed. Thus, the web from the base tape 110, with its longitudinally folded release material (not shown) attached, is joined with a center-line of quick-setting cement to a web of anchoring tape 120, with its longitudinally fold release segments 123 and 125 attached; the two webs move parallel to each other and at the same speed through pressure rolls to unite the webs in a cloth-back to cloth-back relationship. The thus joined webs then pass through a cutting roll or die-cutter which severs successive tape lengths while cutting a scallop 117 from a transverse edge of both webs.

After manufacture of either modification, the severed tape lengths are preferably individually wrapped in a sterile sealed packaging tube of glassine, having a suitable tear-string, as in the packaging of conventional prepared adhesive bandages. The bulk of prepared tapes made according to this invention is so slight, compared to prior art devices, that an ample inventory may be maintained in most facilities. The ability to manufacture prepared tapes embodying this invention from conventional web materials on conventional web-converting and packaging equipment reduces their cost, far below that of prior art devices, to that of conventional prepared adhesive bandages.

The foregoing discloses a preferred and an alternate embodiment of this invention. Other and further modifications may be made by others skilled in the medical profession, medical supply fields, and web-converting fields, for example, without departing from the spirit and scope of the appended claims.

Thus, instead of being the woven cloth of conventional surgical tape, the backings 11 and 21 of the preferred embodiment shown in FIGS. 1 to 3 or in the modification shown in FIG. 9, may be of flexible film, unwoven cloth, or like relative stable flexible material serving as a substrate for the pressure-sensitive adhesive coatings. Likewise, instead of using a narrow strip of cement for joining the base tape and the anchoring tape, stitching or suitable staples may be used for joining these tapes along a narrow area (referred to in the claims as a "linear" area) permitting free flexing of the segments of the anchoring tape around the needle, tube, or similar device desired to be anchored. In the embodiments disclosed, the scallops 17 and 117 have the gently curved sinuous configuration shown in order to minimize the possibility of disturbing an inserted needle as the scalloped transverse edge of the base tape is brought toward and beyond the point of entry. However, instead of this preferred configuration, the of the base tape (and also the anchoring tape, if its length is more than the distance from the bottom of the scallop to the opposite edge of the base tape, as in FIG. 9) may be sharply notched or even simply slit; accordingly, in the appended claims the term "scallop" is to be understood to include any such alternate configuration.

What is claimed is:

1. A prepared tape for securing to a patient's skin or to a support a medical device such as an intravenous needle, a catheter, tubing or the like comprising a length of a flexible base tape and a length of a flexible anchoring tape, each having a pair of lateral edges parallel to its length and opposite adhesive and non-adhesive surfaces, the non-adhesive surface of the base tape being joined to the non-adhesive surface of the anchoring tape in a linear area intermediate of and substantially parallel to the lateral edges of both tapes, whereby, when the base tape is adhered to a supporting surface, a medical device overlying said linear area may be restrained from movement with respect to said supporting surface by adhesion to the surface of segments of the anchoring tape wrapped over said device.

2. A prepared tape as defined in claim 1 in which a transverse edge of the base tape is scalloped adjacent said linear area whereby, when a portion of a needle has been inserted into a patient's skin, the prepared tape, with its scallop opening toward the point of sub-cutaneous entry of the needle may be inserted between the patient's skin and the portion of the needle and any tubing attached thereto which is outside the patient's skin and moved toward the said point of entry until the deepest portion of the scallop nearly touches the needle at said point and the base tape adjacent said scallop, when adhered to the patient's skin, tends to stabilize the patient's skin adjacent said point of entry.

3. A prepared tape as defined in claim 1 in which each adhesive surface of the base and anchoring tapes is covered prior to use with a first strip of release material extending from a first lateral edge toward the opposite second lateral edge and a first pull-tab extending toward said first lateral edge is attached to and overlies said strip of release material adjacent its maximum distance from said first lateral edge, whereby a pull on said first pull-tab will peel back said first strip of release material toward said first lateral edge to expose the adhesive surface theretofore covered by said first strip of release material.

4. A prepared tape as defined in claim 3 in which said pull-tab is an extension of said first strip of release material folded back thereon at a line which constitutes the maximum extent, from said first lateral edge, that the adhesive surface of said tape is covered by said first strip of release material.

5. A prepared tape as defined in claim 3 in which a second strip of release material covers the portion of the adhesive surface not covered by said first strip and extends from the said second lateral edge toward said first strip of release material, and a second pull-tab, extending toward said second lateral edge and overlying said second strip, is attached to said second strip at its maximum distance from said second lateral edge, whereby a pull on said second pull-tab will peel back said second strip of release material toward said second lateral edge to expose the adhesive surface theretofore covered by said second strip of release material.

6. A prepared tape as defined in claim 5 in which said second pull-tab is an extension of said second strip of release material folded back thereon at the line which constitutes the maximum extent, from said second lateral edge, that the adhesive surface of said tape is covered by said second strip of release material.

7. A prepared tape as defined in claim 6 in which the linear area at which the non-adhesive surfaces of the base tape and anchoring tape are joined and the lines at which the pull-tabs are folded back all lie in substantially a single plane which is substantially transverse to the planes of the base tape and anchoring tape and parallel to the lateral edges of said tapes.

8. A prepared tape for securing to a patient's skin or to a support a medical device such as an intravenous needle, a catheter, tubing or the like comprising a length of a flexible base tape and a length of a flexible anchoring tape, each having a pair of lateral edges parallel to its length and opposite adhesive and non-adhesive surfaces, the non-adhesive surface of the base tape being joined to the non-adhesive surface of the anchoring tape in a linear area intermediate of and substantially parallel to the lateral edges of both tapes, but one of the lateral edges of said anchoring tape being closer to said linear area than its parallel lateral edge to provide a shorter segment of anchoring tape, whereby, when the base tape is adhered to a supporting surface, a medical device overlying said linear area may be restrained from movement with respect to said supporting surface by adhesion to the surface of segments of the anchoring tape wrapped over said device.

9. A prepared tape as defined in claim 8 in which a transverse edge of the base tape is scalloped adjacent said linear area whereby, when a portion of a needle has been inserted into a patient's skin, th prepared tape, with its scallop opening toward the point of sub-cutaneous entry of the needle may be inserted between the patient's skin and the portion of the needle and any tubing attached thereto which is outside the patient's skin and moved toward the said point of entry until the deepest portion of the scallop nearly touches the needle at said point and the base tape adjacent said scallop, when adhered to the patient's skin, tends to stabilize the patient's skin adjacent said point of entry.

10. A prepared tape as defined in claim 8 in which a each adhesive surface of the base and anchoring tapes is covered prior to use with a first strip of release material extending from a first lateral edge toward the opposite second lateral edge and a first pull-tab extending toward said first lateral edge is attached to and overlies said strip of release material adjacent its maximum distance from said first lateral edge, whereby a pull on said first pull-tab will peel back said first strip of release material toward said first lateral edge to expose the adhesive surface theretofore covered by said first strip of release material.

11. A prepared tape as defined in claim 10 in which a second strip of release material covers the portion of the adhesive surface not covered by said first strip and extends from the said second lateral edge toward said first strip of release material, and a second pull-tab, extending toward said second lateral edge and overlying said second strip, is attached to said second strip at its maximum distance from said second lateral edge, whereby a pull on said second pull-tab will peel back said second strip of release material toward said second lateral edge to expose the adhesive surface theretofore covered by said second strip of release material.

12. A prepared tape as defined in claim 11 in which said second pull-tab is an extension of said second strip of release material folded back thereon at the line which constitutes the maximum extent, from said second lateral edge, that the adhesive surface of said tape is covered by said second strip of release material.

13. A prepared tape as defined in claim 12 in which the linear area at which the non-adhesive surfaces of the base tape and anchoring tape are joined and the lines at which the pull-tabs are folded back all lie in substantially a single plane which is substantially transverse to the planes of the base tape and anchoring tape and parallel to the lateral edges of said tapes.

* * * * *